(12) United States Patent
Forthmann et al.

(10) Patent No.: US 8,410,448 B2
(45) Date of Patent: Apr. 2, 2013

(54) IMAGING APPARATUS FOR GENERATING AN IMAGE OF A REGION OF INTEREST

(75) Inventors: Peter Forthmann, Sandesneben (DE); Thomas Koehler, Norderstedt (DE); Holger Schmitt, Hamburg (DE)

(73) Assignee: Koninklijke Philips Electronics N.V., Eindhoven (NL)

( * ) Notice: Subject to any disclaimer, the term of this patent is extended or adjusted under 35 U.S.C. 154(b) by 123 days.

(21) Appl. No.: 12/992,285

(22) PCT Filed: May 15, 2009

(86) PCT No.: PCT/IB2009/052038
§ 371 (c)(1),
(2), (4) Date: Nov. 12, 2010

(87) PCT Pub. No.: WO2009/141779
PCT Pub. Date: Nov. 26, 2009

(65) Prior Publication Data
US 2011/0095197 A1    Apr. 28, 2011

(30) Foreign Application Priority Data
May 21, 2008   (EP) .................................. 08156666

(51) Int. Cl.
*G01T 1/16* (2006.01)
(52) U.S. Cl. .................................. 250/370.09; 250/393
(58) Field of Classification Search .................. 250/393, 250/370.09
See application file for complete search history.

(56) References Cited

U.S. PATENT DOCUMENTS

| | | | | |
|---|---|---|---|---|
| 4,590,558 A | * | 5/1986 | Glover et al. | 378/6 |
| 4,709,333 A | * | 11/1987 | Crawford | 600/425 |
| 5,243,664 A | * | 9/1993 | Tuy | 382/130 |
| 6,094,467 A | | 7/2000 | Gayer et al. | |
| 6,721,387 B1 | | 4/2004 | Naidu et al. | |
| 2001/0028696 A1 | | 10/2001 | Yamada et al. | |
| 2004/0066877 A1 | | 4/2004 | Arai et al. | |
| 2005/0123089 A1 | | 6/2005 | Man | |
| 2006/0020200 A1 | | 1/2006 | Medow et al. | |
| 2006/0227928 A1 | | 10/2006 | Timmer | |
| 2007/0008310 A1 | | 1/2007 | Hahn et al. | |

FOREIGN PATENT DOCUMENTS

| | | |
|---|---|---|
| JP | 2005006832 A | 1/2005 |
| WO | 2005076221 A1 | 8/2005 |

(Continued)

OTHER PUBLICATIONS

International Search Report—PCT/IB2009/052038.

(Continued)

*Primary Examiner* — David Porta
*Assistant Examiner* — Marcus Taningco

(57) ABSTRACT

The present invention relates to an imaging apparatus for generating an image of a region of interest. The imaging apparatus comprises a radiation source (2), a detection unit (6) for generating detection data and a moving unit (1, 7, 8) for moving the radiation source (2) and the region of interest relative to each other, while the detection data are generated. The imaging apparatus further comprises an identification unit (13) for identifying in the detection data high density detection data and non-high density detection data. A density weighting unit (14) density weights the detection data, wherein at least a part of the high density detection data has a smaller density weight than the non-high density detection data, and a reconstruction unit (15) reconstructs an image of the region of interest from the weighted detection data.

19 Claims, 4 Drawing Sheets

FOREIGN PATENT DOCUMENTS

WO 2006039809 A1 4/2006

OTHER PUBLICATIONS

Zou et al: "Reduction of the Streak Artifacts in Circular Cone Beam CT Using Scanograms"; 2007 IEEE Nuclear Science Symposium Conference Record, Oct. 1, 2007, pp. 3531-3536.

Koken et al: "Aperture Weighted Cardiac Reconstruction for Cone-Beam CT": Phys. Med. Biology, 2006, vol. 51, pp. 3433-3448.

Bal et al: "Metal Artifact Reduction in CT Using Tissue Class Modeling and Adaptive Prefiltering"; Med. Phys. Aug. 2008, vol. 33, No. 8, pp. 2852-2859.

* cited by examiner

IMAGING APPARATUS FOR GENERATING AN IMAGE OF A REGION OF INTEREST

FIELD OF THE INVENTION

The present invention relates to an imaging apparatus, an imaging method and a computer program for generating an image of a region of interest. The invention relates further to an image generation device, an image generation method and an image generation computer program for generating an image of a region of interest.

BACKGROUND OF THE INVENTION

WO 2006/039809 A1 discloses a computed tomography apparatus being adapted for reducing metal artifacts in a reconstructed image. Projection data are acquired by a detection unit, while a radiation source and the detection unit move along a helical trajectory relative to a patient. A reconstruction unit reconstructs an image of the patient from the acquired projection data and an artifact creating object is determined in this reconstructed image, which can be regarded as a preliminary image. The determined artifact creating object is forward projected onto the detection unit and projection data located within the forward projected artifact creating object are replaced by replacement data, which are calculated by interpolating over projection data outside of the forward projected artifact creating object, thereby producing modified projection data. The modified projection data are used for reconstructing a final image of the patient.

The use of such a computed tomography apparatus has the drawback that the modified projection data are still different to projection data, which would have been measured without the artifact creating object located within the patient, i.e. the modified projection data are still corrupted and produce therefore still artifacts in the final reconstructed image.

SUMMARY OF THE INVENTION

It is an object of the present invention to provide an imaging apparatus, an imaging method and an imaging computer program, wherein high density artifacts, in particular, metal artifacts, in reconstructed images are reduced. It is a further object of the present invention to provide a corresponding image generation device, image generating method and image generation computer program.

In a first aspect of the present invention an imaging apparatus for generating an image of a region of interest is presented, wherein the imaging apparatus comprises:
- a radiation source for generating radiation for traversing the region of interest,
- a detection unit for generating detection data, which depend on the radiation after having traversed the region of interest,
- a moving unit for moving the radiation source and the region of interest relative to each other, while the detection data are generated,
- an identification unit for identifying in the detection data high density detection data, which depend on radiation, which has traversed a high density region having a density larger than a predefined density, and for identifying non-high density detection data, which depend on radiation, which has not traversed the high density region,
- a density weighting unit for density weighting the detection data, wherein at least a part of the high density detection data has a smaller density weight than the non-high density detection data,
- a reconstruction unit for reconstructing an image of the region of interest from the weighted detection data.

The invention is based on the idea that high density detection data, i.e. detection data which could be corrupted because the corresponding radiation has passed the high density region, are less density weighted than the non-high density detection data. Thus, high density artifacts in reconstructed images are reduced by reducing the influence of detection data, which are likely to be corrupted, i.e. high density detection data, thereby reducing high density artifacts, in particular, metal artifacts, in the reconstructed image. The high density region is preferentially a metallic region within the region of interest. If a patient having metallic implants is located within the region of interest, the identification unit is preferentially adapted to identify the location, the shape and the dimensions of the metallic implant within the region of interest. The predefined density is preferentially chosen such that the identification unit identifies high density detection data, which depend on radiation, which has traversed a metallic region, and non-high density detection data, which depend on radiation, which has not traversed the metallic region.

One or several high density regions can be present, wherein the identification unit is preferentially adapted to identify high density detection data, which depend on radiation, which has traversed at least one of the several high density regions, and to identify non-high density detection data, which depend on radiation, which has not traversed any of the high density regions.

In a preferred embodiment, the density weighting unit is adapted such that all high density detection data have a smaller density weight than the non-high density detection data. In a further preferred embodiment, at least a part or all of the high density detection data are density weighted with a zero value, wherein at least a part or all of the non-high density detection data are density weighted with a non-zero value. If all high density detection data are density weighted with a zero value, high detection data, which might be corrupted, are not used by the reconstruction unit for reconstructing an image of the region of interest, thereby further reducing high density artifacts in the reconstructed image.

The density weighting unit is a weighting unit, which weights the detection data depending on the identification whether a detection data belongs to high-density detection data or to non-high density detection data. The corresponding weighting, weight and weighting factor is indicated by density weight, density weighting and density weighting factor, respectively.

The reconstruction unit is preferentially adapted to use a backprojection for reconstructing an image of the region of interest from the weighted detection data.

In a preferred embodiment, the radiation has the shape of a cone beam. This cone-beam shape allows to radiate a region behind a high density region, i.e. on a side of the high density region opposite to a location, at which the radiation source is located. Thus, even an image of a region behind a high density region could be reconstructed by the reconstruction unit.

It is further preferred that the imaging apparatus further comprises an aperture weighting unit for aperture weighting the detection data. This aperture weighting is preferentially performed such that detection data, which correspond to rays which are centrally located within the cone, obtain a higher aperture weight than more peripheral rays. In particular, detection data, which correspond to rays, which are more peripheral with respect to an intersection of the cone-beam and a plane, which traverses the radiation source position and in which the rotational axis is completely located, if the radiation source and the region of interest are rotated relative to each other by the moving unit, obtain a lower aperture weight than detection data, which correspond to rays, which are located more centrally within this intersection. A more detailed description of this aperture weighting is disclosed in the article "Aperture weighted cardiac reconstruction for cone-beam CT" by P. Koken and M. Grass, 3433-3448, Phys. Med. Biol. 51 (2006), which is herewith incorporated by reference. The aperture weighting further reduces artifacts, which can be generated, if different cone angles of different rays are not considered, and, thus, improves the quality of the reconstructed image.

It is further preferred that the reconstruction unit is adapted to perform a cone-beam reconstruction, in particular, and an aperture weighted cone-beam reconstruction, wherein the divergence of the rays in the cone angle direction is considered, wherein if, for example, the moving unit rotates the radiation source and the region of interest relative to each other around a rotational axis, the cone angle is defined as an angle between a first line, which is perpendicular to the rotational axis and which traverses the radiation source location, and a second line defining a ray, which is located within a plane parallel or identical to a plane defined by the first line and the rotational axis. This consideration of the cone angle improves the quality of the reconstructed image. For a detailed description of an aperture weighted cone-beam reconstruction reference is made to the above-mentioned article by Koken et al.

The moving unit can be adapted to move the radiation source only, wherein the region of interest is not moved, to move the region of interest only, wherein the radiation source is not moved or to move both, the radiation source and the region of interest. For example, the radiation source can be rotated around the region of interest such that the radiation source is moved along a circular trajectory around the region of interest. The radiation source and the region of interest can be moved relative to each other along a helical trajectory, if, for example, the radiation source is rotated around the region of interest and if the region of interest is linearly moved, for example, by moving a patient located on a patient table linearly. Furthermore, the radiation source or the region of interest can be moved linearly such that the radiation source and the region of interest move relative to each other along a linear trajectory.

It is further preferred that the density weighting unit is adapted to multiply the detection data with density weighting factors, which depend on the line integral through the high density region along a line from the radiation source to the respective detection datum, wherein the density weighting factor is larger, if the line integral is smaller. In particular, only values within the high density region contribute to the respective line integral. The high-density region can, for example, be determined by reconstructing a preliminary image of the region of interest and by segmenting the high density region within the preliminary image, wherein the image values, in particular, Hounsfield values, are used for calculating the respective line integral.

It is further preferred that the imaging apparatus further comprises a high density region determination unit for determining the high density region. Preferentially, the radiation source, the detection unit and the moving unit are adapted to acquire a scanogram and the high density region determination unit is adapted to determine the high density region from the scanogram. Preferentially, in addition, the high density determination unit further considers knowledge about the typical anatomy of an object within the region of interest to determine the high density region, in particular, the location, shape and dimensions of the high density region. For example, at least two scanograms can be acquired from different directions in order to achieve depth information and in order to estimate the location, the shape and the dimensions of the high density region from these at least two scanograms. Furthermore, a model of the object located in the region of interest can be registered with respect to the at least two scanograms, wherein the location of the high density region with respect to the model and the shape and the dimensions of the high density region are not known, for example, from previous measurements or because it is known that the high density region is formed by a certain metallic object, for example, a certain metallic prosthesis. It is further preferred that the high density region determination unit is adapted to reconstruct a preliminary image of the region of interest from the detection data and to segment the high density region in the preliminary image for determining the high density region.

It is further preferred that the identification unit is adapted to forward project the determined high density region and to identify non-high density detection data as detection data outside the forward projected high density region and to identify high density detection data as detection data inside the forward projected high density region. This allows to accurately identify high density detection data and non-high density detection data.

It is further preferred that the moving unit is adapted to move the radiation source and the region of interest relative to each other along a helical trajectory, wherein the high density region is located off-center with respect to a central longitudinal axis of the helical trajectory, wherein the helical trajectory is adapted such that the high density region is longitudinally centered with respect to portions of windings of the helical trajectory having the shortest distance to the high density region. This reduces the fraction of high detection data of the detection data such that the fraction of detection data, which obtain a small density weight with respect to the density weight of non-high detection data or which are not used during the reconstruction, is reduced, thereby reducing unnecessary radiation dose applied on the region of interest, in particular, if a patient is located within the region of interest, on a patient.

In a further aspect of the present invention an image generation device for generating an image of a region of interest as presented, the detection data being dependent on radiation after having traversed the region of interest, the radiation for traversing the region of interest being generated by a radiation source, the radiation source and the region of interest being moved relative to each other, while the detection data are generated, wherein the image generation device comprises:

an identification unit for identifying in the detection data high density detection data, which depend on radiation, which has traversed a high density region having a density larger than a predefined density, and for identifying in the detection data non-high density detection data, which depend on radiation, which has not traversed the high density region, a density weighting unit for density weighting the detection data, wherein at least a part of the high density detection data has a smaller density weight than the non-high density detection data, a reconstruction unit for reconstructing an image of the region of interest from the weighted detection data.

In a further aspect of the present invention an imaging method for generating an image of a region of interest is presented, wherein the imaging method comprises following steps:

generating radiation for traversing the region of interest by a radiation source, generating detection data, which depend on the radiation after having traversed the region of interest, moving the radiation source and the region of interest relative to each other, while the detection data are generated, identifying in the detection data high density detection data, which depend on radiation, which has traversed a high density region having a density larger than a predefined density, and non-high density detection data, which depend on radiation, which has not traversed the high density region, density weighting the detection data, wherein at least a part of the high density detection data has a smaller density weight than the non-high density detection data, reconstructing an image of the region of interest from the weighted detection data.

In a further aspect of the present invention an image generation method for generating an image of a region of interest is presented, the detection data being dependent on radiation after having traversed the region of interest, the radiation for traversing the region of interest being generated by a radiation source, the radiation source and the region of interest being moved relative to each other, while the detection data are generated, wherein the image generation method comprises following steps:

identifying in the detection data high density detection data, which depend on radiation, which has traversed a high density region having a density larger than a predefined density, and identifying non-high density detection data, which depend on radiation, which has not traversed the high density region, density weighting the detection data, wherein at least a part of the high density detection data has a smaller density weight than the non-high density detection data, reconstructing an image of the region of interest from the weighted detection data.

In a further aspect of the present invention an imaging computer program for generating an image of a region of interest is presented, wherein the computer program comprises program code means for causing an imaging apparatus as defined in claim 1 to carry out the steps of the imaging method as defined in claim 10, when the imaging computer program is run on a computer controlling the imaging apparatus.

In a further aspect of the present invention an image generation computer program for generating an image of a region of interest is presented, wherein the computer program comprises program code means for causing an image generation device as defined in claim 9 to carry out the steps of the image generation method as defined in claim 11, when the image generation computer program is run on a computer.

It shall be understood that the imaging apparatus of claim 1, the image generation device of claim 9, the imaging method of claim 10, the image generation method of claim 11 and the computer programs of claims 12 and 13 have similar and/or identical preferred embodiments as defined in the dependent claims.

It shall be understood that a preferred embodiment of the invention can also be any combination of the dependent claims with a respective independent claim.

BRIEF DESCRIPTION OF THE DRAWINGS

These and other aspects of the invention will be apparent from and elucidated with reference to the embodiments described hereinafter. In the following drawing.

DETAILED DESCRIPTION OF EMBODIMENTS

Figure 1:
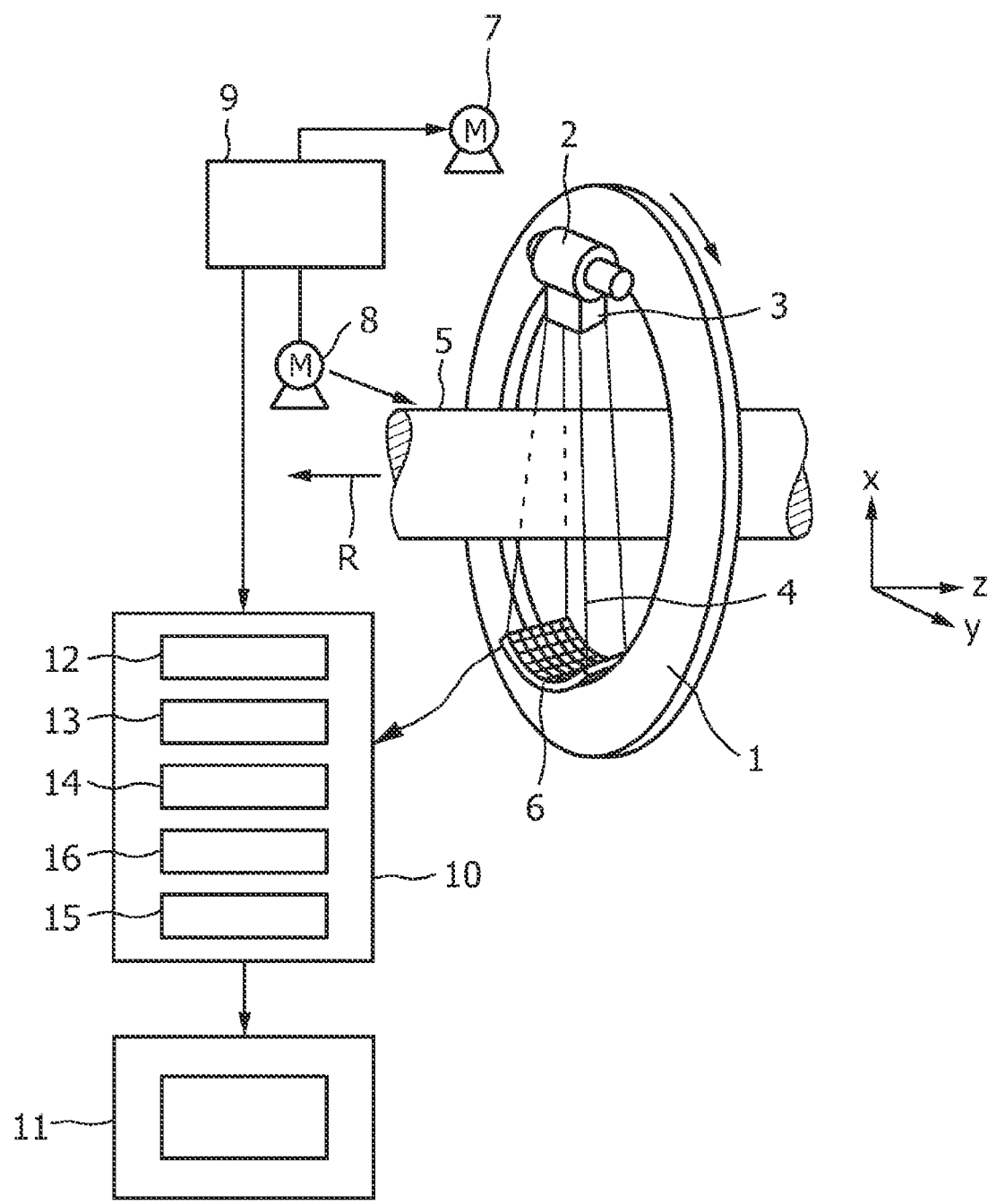
FIG. 1 shows schematically and exemplarily an embodiment of an imaging apparatus for generating an image of a region of interest.

FIG. 1 shows schematically and exemplarily an imaging apparatus for generating an image of a region of interest being, in this embodiment, a computed tomography apparatus. The computed tomography apparatus includes a gantry 1, which is capable of rotation about a rotational axis R, which extends parallel to the z direction. A radiation source 2, which is, in this embodiment, an X-ray tube, is mounted on the gantry 1. The radiation source 2 is provided with a collimator 3, which forms, in this embodiment, a conical radiation beam 4 from the radiation generated by the radiation source 2. The radiation traverses an object (not shown), such as a patient, and a region of interest, which is preferentially located within the object, in an examination zone 5, which is, in this embodiment, cylindrical. After having traversed the examination zone 5 the radiation beam 4 is incident on the detection unit 6, which comprises, in this embodiment, a two-dimensional detection surface. The detection unit 6 is mounted on the gantry 1.

The computed tomography apparatus comprises two motors 7, 8. The gantry 1 is driven at a preferably constant but adjustable angular speed by the motor 7. The motor 8 is provided for displacing the object and, thus, the region of interest, wherein the object is, for example, a patient, who is arranged on a patient table in the examination zone 5, parallel to the direction of the rotational axis R or the z axis. These motors 7, 8 are controlled by a control unit 9, for instance, such that the radiation source 2 and the examination zone 5 and, thus, the region of interest within the examination zone move relative to each other along a helical trajectory. However, it is also possible that the object or the examination zone 5 is not moved, but that only the radiation source 2 is rotated, i.e. that the radiation source 2 moves along a circular trajectory relative to the object or the examination zone 5, i.e. relative to the region of interest. Furthermore, in another embodiment, the collimator 3 can be adapted for forming another beam shape, in particular, a fan beam, and the detection unit 6 can comprise a detection surface, which is shaped corresponding to the other beam shape, in particular, to the fan beam.

During a relative movement of the radiation source and the region of interest the detection unit 6 generates detection data, which are, in this embodiment, projection data and which depend on the radiation incident on the detection surface of the detection unit 6. Therefore, the radiation source 2 and the elements for moving the radiation source 2 and the region of interest relative to each other, in particular, the motor 7, 8 and the gantry 1, form a moving unit for moving the radiation source and the region of interest relative to each other.

The detection data are provided to an image generation device 10 for generating an image of the region of interest from detection data, i.e., in this embodiment, from the projection data. The region of interest is located within the examination zone and preferentially contains an object or a part of an object. The image generation device 10 comprises an identification unit 13 for identifying in the detection data high density detection data, which depend on radiation, which has traversed a high density region having a density larger than a predefined density, and for identifying in the detection data non-high density detection data, which depend on radiation, which has not traversed the high density region. The image generation device further comprises a density weighting unit 14 for density weighting the detection data, wherein at least a part of the high density detection data has a smaller density weight than the non-high density detection data, and a reconstruction unit 15 for reconstructing an image of the region of interest from the weighted detection data. In this embodiment, the image generation device 10 further comprises a high density region determination unit 12 for determining the high density region, in particular, for determining the location, the shape and/or the dimensions of the high density region, and an aperture weighting unit 16 for aperture weighting the detection data.

Preferentially, the high density region determination unit 12 is adapted to reconstruct a preliminary image of the region of interest from the detection data and to segment the high density region in the preliminary image for determining the high density region.

The high density region is defined as a region comprising density values above a predefined density. This predefined density is, for example, larger than 1000 Hounsfield units, preferentially larger than 1100 Hounsfield units and it is further preferred that the predefined density is equal or close to 1200 Hounsfield units. In particular, the predefined density is preferentially chosen such that a metallic region comprises a density larger than the predefined density. The metallic region is, for example, a metallic implant in a head of a patient, for example, a metallic filling in a tooth.

Since in an embodiment the preliminary image is used for segmenting the high density region in the preliminary image, the high density region determination unit 12 is preferentially adapted to reconstruct the preliminary image with a lower quality than a final image, i.e., for example, with a lower spatial resolution, with a smaller signal-noise ratio and/or with more artifacts than in the final reconstructed image.

The high density region in the image can be segmented by, for example, global thresholding, i.e. defining all voxels above a certain threshold (1200 HU, for example) as belonging to the high density object, and others not. An alternative segmentation method is k-means clustering, which can identify the high density region on the basis of the image histogram without a pre-defined threshold. The k-means clustering is, for example, disclosed in the article "Metal artifact reduction in CT using tissue-class modeling and adaptive prefiltering", M. Bal and L. Spies, Med. Phys., 33 (8):2852-2859, 2006, which is herewith incorporated by reference.

The high density region determination unit 12 can also be adapted to determine the high density region from a scanogram. A scanogram is a projection image of the examination zone, which contains at least the region of interest. The scanogram gives an overview and is generally used for planning a computed tomography scan for acquiring detection data by the detection unit, while the radiation source and the region of interest move relative to each other. The scanogram can be generated by moving the radiation source and the region of interest linearly to each other, for example, by moving a patient table, on which a patient is located, linearly, in particular, in the direction of the z axis or the rotational axis R, with respect to the radiation source, which is not moving. In other embodiments, the scanogram can be generated in an other way. For example, scanogram detection data can be acquired, while the radiation source generates low intensity radiation and the radiation source and the region of interest move relative to each other along a helical trajectory. Low intensity radiation means that the intensity of the radiation is lower than the intensity of the radiation, which is used for a following generation of detection data, which are used for reconstructing the final image of the region of interest. The scanogram detection data can be used for reconstructing a low quality image of the region of interest, and a scanogram can be generated by simulating a forward projection through the low quality image.

If the high density region determination unit is adapted to determine the high density region from the scanogram, preferentially, in addition, the high density determination unit 12 is adapted to further consider knowledge about a typical structure of an object within the region of interest, in particular, about the typical anatomy of a patient, for determining the high density region, in particular, the location, the shape and dimensions of the high density region. For example, if it is known that the high density region is a metallic filling in a certain tooth of a patient and if the positioning of the patient on the patient table is known, this can be used together with the scanogram to determine the high density region.

The identification unit 13 is preferentially adapted to forward project the high density region, which is preferentially determined by the high density region determination unit 12, and to identify non-high density detection data as detection data outside the forward projected high density region and to identify high density detection data as detection data inside the forward projected high density region. Preferentially, the identification unit 14 is adapted to interpolate the detection data.

In particular, preferentially the high density detection data are replaced by interpolated detection data, wherein in the following steps these interpolated detection data are regarded as being the high density detection data. In an embodiment, the detection unit comprises detection elements, which are arranged along lines. Interpolated detection values along these lines are calculated for the parts of the lines, which are within a high density region, by interpolation, in particular, linear interpolation, using preferentially only the two detection data values, which are directly adjacent to the part of the respective line of the detection unit, along which interpolated value have to be calculated.

The density weighting unit 14 is preferentially adapted to multiply the detection data with density weighting factors, which depend on the line integral through the high density region along a line from the radiation source 2 to the respective detection datum, wherein the density weighting factor is larger, if the line integral is smaller. In particular, only values within the high density region contribute to the respective line integral. If, for example, the high density region has been determined by reconstructing a preliminary image of the region of interest and by segmenting the high density region within the preliminary image, the line integrals are calculated based on the image values, in particular, the Hounsfield values, within the high density region only.

In a preferred embodiment, the density weighting factor $w_{hd}$ is set to $$w_{hd} = \begin{cases} a : l < b \\ \frac{1}{l} : b \leq l \leq c \\ d : l > e \end{cases} \quad (1)$$

wherein l is the line integral through the high density region and wherein preferentially b is smaller than c, e is equal to or larger than c, a is larger than d and 1/l, and d is smaller than a and optionally 1/l. In another embodiment, $w_{hd}$ is equal to zero for all high density detection data and non-zero for all non-high density detection data. The values a, b, c, d, e are preferentially chosen such that high density artifacts in the reconstructed image are further, in particular, optimally, reduced. This can be done by determining optimal values a, b, c, d, e by choosing the same such that in images of corresponding training data sets high density artifacts are optimally reduced, in particular, eliminated. In a preferred embodiment, a is equal to 100, b is equal to 0.01, c is equal to 6, d is equal to ⅙ and e is equal to 6. If the density weighting factors $w_{hd}$ are chosen as in equation (1), the non-high density detection data obtain preferentially a density weighting factor equal to or larger than a.

The aperture weighting unit 16 is adapted to perform an aperture weighting on the detection data, wherein detection data, which correspond to rays, which are more centrally within a cone with respect to a cone angle direction, obtain a larger aperture weight than detection data, which correspond to rays, which are located more peripheral within the cone in the cone angle direction. A more detailed description of this aperture weighting is disclosed in the above-mentioned article by Koken et al., which is herewith incorporated by reference.

The reconstruction unit 15 is adapted to reconstruct an image of the region of interest, in particular, a final image, by using a cone-beam reconstruction. A cone-beam reconstruction is a reconstruction algorithm, which considers the divergence of the rays in the cone angle direction. An example of such a cone-beam reconstruction is disclosed in the above-mentioned article by Koken et al. In other embodiments, the reconstruction unit can be adapted to reconstruct an image of the region of interest using another reconstruction algorithm, in particular, using another cone-beam reconstruction algorithm.

Figure 2:
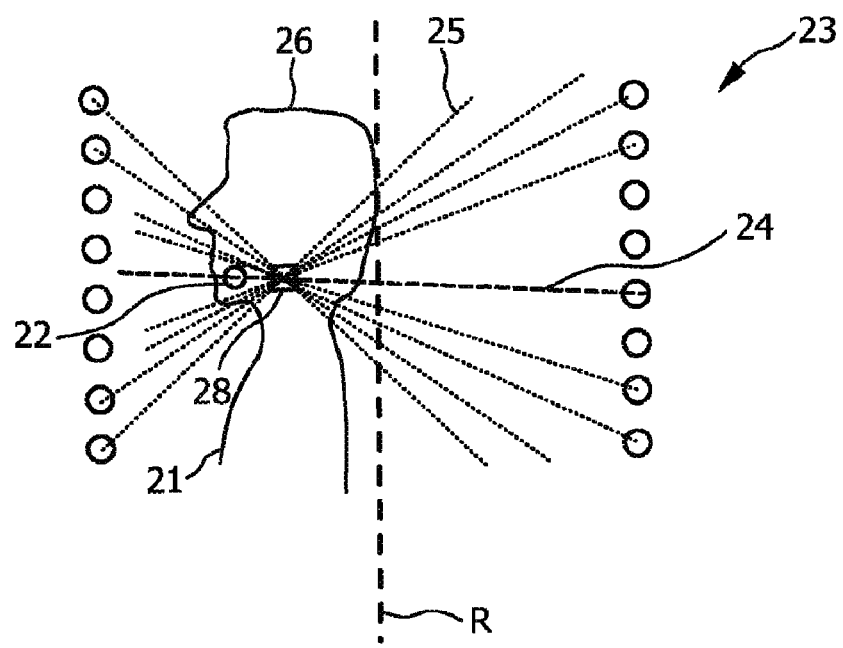
FIGS. 2 to 4 show schematically and exemplarily different acquisition geometries.

FIG. 2 shows schematically and exemplarily an acquisition geometry for acquiring detection data, which illustrates high density rays, which correspond to high density detection data, and non-high density rays, which correspond to non-high density detection data.

A head 26 of a patient 21 is located within an examination zone within the region of interest. This circles in FIG. 2 indicate a helical trajectory 23, along which the radiation source and the region of interest are moved relative to each other. In this example, the voxel 28 has to be reconstructed and rays 24, 25 are shown, which traverse this voxel 28. The ray 24 has traversed a high density region 22, which can be a metallic filling in a tooth. This ray is regarded as a high density ray. The rays 25, which traverse the voxel 28, but which do not traverse the high density region 22, can be regarded as non-high density rays, which correspond to non-high detection data, whereas the high density rays correspond to high density detection data. During backprojection, which is preferentially performed in this embodiment for reconstructing an image of the region of interest, the high density detection data obtain a lower density weight than non-high density detection data. In particular, the density weight of the non-high density detection data can be a zero value such that the high density detection data are not considered during reconstructing the image.

Figure 3:
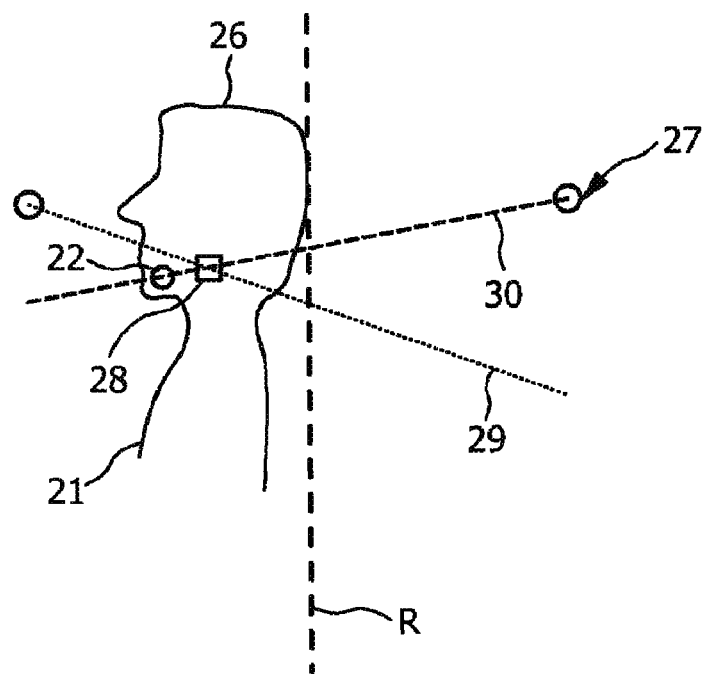

FIG. 3 shows schematically and exemplarily a further acquisition geometry, wherein the radiation source moves along a circular trajectory 27 with respect to the region of interest. A patient 21 is located on a patient table such that the head 26 of the patient is located within the region of interest. The line 29 indicates a ray, which traverses the voxel 28, but which does not traverse the high density region 22. This ray is a non-high density ray, which corresponds to non-high detection data. The dashed line 30 indicates a high density ray, which traverses the voxel 28 and the high density region 22 and which corresponds to high density detection data.

Figure 4:
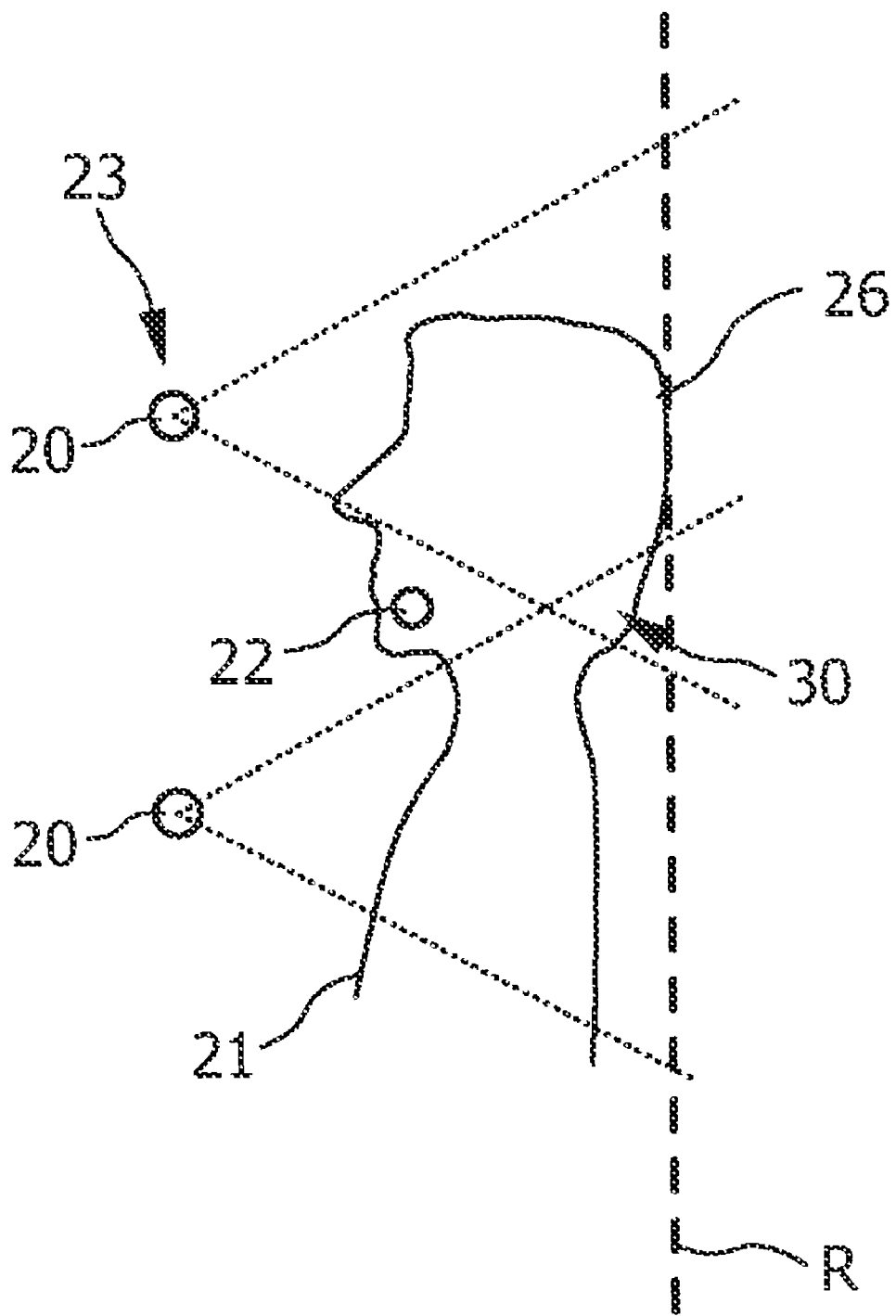

FIG. 4 shows schematically and exemplarily a preferred acquisition geometry for acquiring detection data, wherein the moving unit moves the radiation source and the region of interest relative to each other along a helical trajectory 23. From this helical trajectory only two portions 20 of windings of the helical trajectory 23 are shown, which have the shortest distance to the high density region 22. In this preferred acquisition geometry the high density region 22 is located off-centre with respect to a central longitudinal axis of the helical trajectory, which is, in this embodiment, the rotational axis R. Thus, preferentially an object is arranged such that a high density region, for example, a filling within a tooth of a patient, is located off-centre with respect to the central longitudinal axis of the helical trajectory within the examination zone. The location, shape and/or dimensions of the high density region 22 can be known in advance or can be determined, for example, by the above described high density region determination unit.

In a preferred embodiment an object, in particular, a patient with dental fillings or implants is positioned such that the high density region is located off-centre with respect to a central longitudinal axis of the helical trajectory. For example, a patient is positioned such that the nose is pointing towards the gantry 1. This can be achieved either with the patient lying face-up on the table and above the central longitudinal axis of the helical trajectory or lying face-down below the central longitudinal axis of the helical trajectory. Then, the high density region is determined as described above by the high density determination unit. In particular, a scanogram, preferentially a two-dimensional scanogram, is acquired to locate the high density region. The high density determination unit determines then the high density region, in particular, the location, the shape and the dimensions, based on the acquired scanogram and the position of the patient table and knowledge about the typical anatomy, in particular, by estimating the approximate location of the high density region in three-dimensional space.

The imaging apparatus, in particular, the moving unit, is preferentially adapted to arrange a helical trajectory, along which the radiation source and the region of interest move relative to each other, such that the outside edge of the high density region, i.e. the outside edge of the high density region, which is off-centre with respect to the central longitudinal axis of the helical trajectory and which has the smallest distance to this axis, is in the middle of two portions 20 of the windings of the helical trajectory 23, i.e. in the middle of the radiation source positions on these portions 20. If the helical trajectory and the high density region are arranged with respect to each other in this way, the area 30 "behind" the high density region 22 is optimally irradiated while minimizing the number of rays that are density weighted with a relatively small density weighting factor or that are discarded. The area 30 "behind" the high density region 22 is an area, which is located on the opposite side of the high density region 22 with respect to the side, at which the portions 20 of the windings of the helical trajectory 23 are located.

This positioning of an object within the region of interest such that the high density region is located off-centre with respect to a central longitudinal axis of the helical trajectory, wherein the helical trajectory is adapted such that the high density region is longitudinally centred with respect to portions of windings of the helical trajectory having the shortest distance to the high density region, minimises unnecessary radiation. This positioning and the following density weighting by the density weighting unit, the optional aperture weighting by the aperture weighting unit and the reconstructing by the reconstruction unit is preferentially applied to helical or circular head/neck computed tomography scans that could suffer from metal artifacts.

The above mentioned preferred positioning of the helical trajectory and the high density region with respect to each other is preferentially achieved by determining a corresponding optimal start position of the radiation source, at which the radiation source starts to emit radiation, if the radiation source and the region of interest move relative to each other along the helical trajectory. This optimal start position can easily be calculated if the cone angle of the radiation, the pitch of the helical trajectory, i.e. the distance between two neighboured windings of the helical trajectory, and the location of the high density region are known. The region immediately "behind" the high density region 22 is a non-reconstructable area. In order to keep this non-reconstructable area small, the pitch of the helical trajectory is small in a preferred embodiment, i.e. if the non-reconstructable area should be smaller than a desired area value, the pitch of the helical trajectory has to be chosen such that the non-reconstructable area is not larger than this desired area value. This is easily possible, if the acquisition geometry and the position, shape and dimensions of the high density region are known.

Referring again to the density weighting unit, aperture weighting unit and the reconstruction unit, preferentially pi-partners are used in an reconstruction algorithm executed by the reconstruction unit and optionally in addition by the aperture weighting unit. Pi-partners are detection data, which correspond to rays, which are located on the same straight line intersecting the voxel, which has to be reconstructed, and radiate in opposite directions. The identification unit can be adapted for identifying high density pi-partners detection data and non-high density pi-partners detection data, wherein the weighting unit is adapted to give the non-high density pi-partners detection data a larger density weight than the high density pi-partners detection data. In particular, the high density pi-partners detection data are weighted with a zero value and the none-high density pi-partners detection data are weighted with a non-zero value, i.e. the high density pi-partners detection data can be discarded and are not used for reconstruction.

A preferred reconstruction algorithm using pi-partners, which can be used by the reconstruction unit, is, for example, disclosed in the above-mentioned article by Koken et al., which is herewith incorporated by reference.

Figures 5, 6:
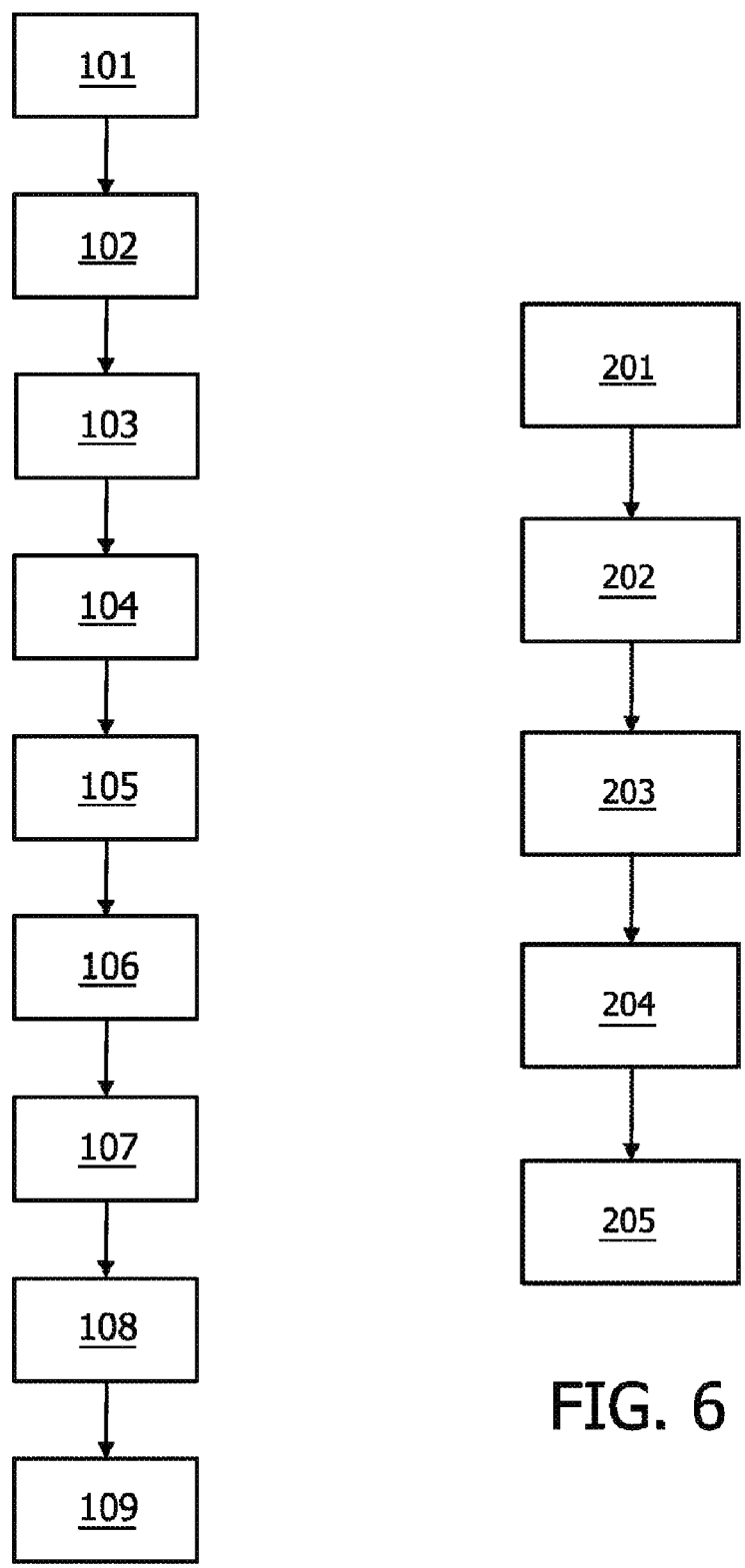
FIG. 5 shows exemplarily a flow chart illustrating an embodiment of an imaging method for generating an image of a region of interest and FIG. 6 shows exemplarily a flow chart illustrating an embodiment of an image generation method for generating an image of a region of interest.

In the following an embodiment of an imaging method for generating an image of a region of interest will be illustrated with reference to a flow chart shown in FIG. 5.

In step 101, an object, in particular, a patient, is positioned within the region of interest such that a high density region is located off-centre with respect to a central longitudinal axis of a helical trajectory, along which the radiation source and the region of interest will move relative to each other.

Then, in step 102, the high density region is determined by the high density region determination unit, for example, by using a scanogram which can be acquired after step 101 and before step 102, and knowledge about the structure of the object, in particular, the typical anatomy of a patient. In addition, if a patient is located on a patient table, the position of the patient table can be used for determining the high density region.

In step 103, the helical trajectory is arranged such that the high density region is located off-centre with respect to a central longitudinal axis of the helical trajectory, wherein the helical trajectory is adapted such that the high density region is longitudinally centred with respect to portions of windings of the helical trajectory having the shortest distance to the high density region. In particular, the helical trajectory is arranged such that an outer edge of the high density region having the shortest distance to the helical trajectory is located off-centre with respect to the central longitudinal axis of the helical trajectory, wherein the helical trajectory is adapted such that the high density region and/or this outer edge of the high density region is longitudinally centred with the respect to the portions of windings of the helical trajectory having the shortest distance to this outer edge of the high density region. This is preferentially performed by determining the optimal start position of the radiation source, if the cone angle of the radiation beam and the pitch of the helical trajectory and the location of the high density region are known. In step 104, detection data are generated, i.e. detection data are acquired, while the radiation source moves relative to the region of interest along the helical trajectory, which has been determined in step 103.

After the detection data have been acquired, in the detection data high density detection data, which depend on radiation, which has traversed the high density region, and non-high density detection data, which depend on radiation, which has not traversed the high density region, are identified in step 105. This identification is preferentially performed by forward projecting the high density region and determining, which detection data are within the forward projected high density region and which detection data are outside the forward projected high density region.

Optionally, in step 106, the detection data are interpolated, in particular, linearly interpolated as described above.

In step 107, the detection data are density weighted, wherein at least a part of the high density detection data obtain a smaller density weighting factor than the non-high density detection data. Preferentially, the high density detection data are density weighted with a zero value and the non-high density detection data are density weighted with a non-zero value.

Preferentially, in step 108, the density weighted detection data are, in addition, aperture weighted.

In step 109, the detection data are used for reconstructing an image for the region of interest, in particular, the detection data are backprojected, wherein preferentially a cone-beam reconstruction is used, which is, for example, disclosed in the above-mentioned article by Koken et al.

In the following an embodiment of an image generation method for generating an image of a region of interest will be described with reference to a flow chart shown in FIG. 6.

The image generation method is adapted to generate an image of a region of interest from detection data, wherein the detection data depend on radiation after having traversed the region of interest, wherein the radiation is generated by a radiation source and wherein the radiation source and the region of interest are moved relative to each other, while the detection data are generated.

In step 201, in the detection data high density detection data, which depend on radiation, which has traversed a high density region having a density larger than a predefined density, and non-high density detection data, which depend on radiation, which has not traversed the high density region, are identified. Optionally, in step 202, the detection data are interpolated, in particular, linearly interpolated. In step 203, the detection data are density weighted, wherein at least a part of the high density detection data obtains a smaller density weight than the non-high density detection data. In step 204, the detection data are preferentially aperture weighted. In step 205, the detection data are used for reconstructing an image of the region of interest. Steps 201 to 205 correspond to steps 105 to 109. For a more detailed description of steps 201 to 205 reference is therefore made to the above description of steps 105 to 109.

High density artifacts in reconstructed images are mainly caused by a non-linear attenuation of radiation by different materials. This generally leads to beam hardening. Since detection data, which are effected by this beam hardening, obtain a lower density weight than other detection data or are even discarded, high density artifacts in the reconstructed image are reduced.

Although in the above described embodiments the position of the high density region is automatically detected by using a scanogram, the high density region can also be determined by a user, who sees the high density region on the scanogram and who can manually position an object, for example, a patient on a patient table, such that the high density region is located off-centre with respect to the central longitudinal axis. Furthermore, the user can indicate the high density region on the scanogram and the indicated high density region can be used for estimating the position, shape and/or dimensions of the high density region, wherein a helical trajectory is adapted such that the high density region is longitudinally centred with respect to portions of windings of the helical trajectory having the shortest distance to the high density region.

Although in the above described embodiments the high density region has been determined by using the scanogram for adapting the helical trajectory such that the high density region is located off-centre with respect to a central longitudinal axis of the helical trajectory, in other embodiments, the position, shape and/or dimensions of the high density region can be known from, for example previous measurements or can be determined by another method, for example, by performing a computed tomography acquisition of preliminary detection data, which are used for reconstructing an preliminary image of the region of interest, wherein the high density region can be determined by segmenting the same in the preliminary image of the high density region.

Although in the above described embodiments the imaging apparatus is preferentially a computed tomography apparatus, in particular, an X-ray computed tomography apparatus, in other embodiments, other imaging apparatuses can be used, for example, an C-arm apparatus, a magnetic resonance imaging apparatus, an ultrasonic imaging apparatus or a nuclear imaging apparatus, like a single photon emission computed tomography apparatus or a positron emission tomography apparatus.

Although in the above described embodiments the object is preferentially a head of a patient and the high density region is preferentially a metallic filling or a metallic implant, in other embodiments, an image of another part of a human or animal patient can be reconstructed, wherein the high density region is preferentially a metallic element within the patient.

In a further embodiment, the imaging apparatus can be adapted to image technical objects.

Although in the above described embodiments the trajectory, along which the radiation source and the region of interest are moved relative to each other, is preferentially a helical trajectory, in other embodiments the radiation source and the region of interest can move relative to each other along another trajectory, for example, along a circular trajectory or along a linear trajectory.

Other variations to the disclosed embodiments can be effected by those skilled in the art in practicing the claimed invention, from a study of the drawings, the disclosure, and the appended claims.

In the claims the word "comprising" does not exclude other elements or steps, and the indefinite article "a" or "an" does not exclude e plurality.

A single unit or device may fulfill the functions of several items recited in the claims. The mere fact that certain measures are recited in mutually different dependent claims does not indicate that a combination of this measures cannot be used to advantage.

Determinations, identifications, calculations, reconstructions et cetera performed by one or several units or devices can be performed by any other number of units or devices. For example, steps 105 to 109 or steps 201 to 205 can be performed by a single unit or by any other number of different units. The identifications, reconstructions, determinations, calculations et cetera and/or the control of the imaging apparatus and/or of the image generation device in accordance with the above described imaging method and/or image generation method can be implemented as program code means of a computer program and/or as dedicated hardware.

A computer program may be stored/distributed on a suitable medium, such as an optical storage medium or a solid-state medium, supplied together with or as part of other hardware, but may also be distributed in other forms, such as via the internet or other wired or wireless telecommunication systems.

Any reference signs in the claims should not be construed as limiting the scope.

The invention claimed is:

1. An imaging apparatus for generating an image of a region of interest, the imaging apparatus comprising:
    a radiation source for generating radiation for traversing the region of interest, a detection unit for generating detection data, which depend on the radiation after having traversed the region of interest,
    a moving unit for moving the radiation source and the region of interest relative to each other, while the detection data are generated,
    an identification unit for identifying in the detection data high density detection data, which depend on radiation, which has traversed a high density region having a density larger than a predefined density, and for identifying non-high density detection data, which depend on radiation, which has not traversed the high density region,
    a density weighting unit for density weighting the detection data, wherein at least a part of the high density detection data has a smaller density weight than the non-high density detection data,
    a reconstruction unit for reconstructing an image of the region of interest from the weighted detection data.

2. The imaging apparatus as defined in claim 1, wherein the radiation has the shape of a cone beam.

3. The imaging apparatus as defined in claim 1, wherein the density weighting unit multiplies the detection data with density weighting factors, which depend on the line integral through the high density region along a line from the radiation source to the respective detection datum, wherein the density weighting factor is larger, if the line integral is smaller.

4. The imaging apparatus as defined in claim 1, wherein the imaging apparatus further comprises a high density region determination unit for determining the high density region.

5. The imaging apparatus as defined in claim 4, wherein the radiation source, the detection unit and the moving unit acquires a scanogram and the high density region determination unit determines the high density region from the scanogram.

6. The imaging apparatus as defined in claim 4, wherein the high density region determination unit reconstructs a preliminary image of the region of interest from the detection data and to segment the high density region in the preliminary image for determining the high density region.

7. The imaging apparatus as defined in claim 4, wherein the identification unit forward projects the determined high density region and identifies non-high density detection data as detection data outside the forward projected high density region and identifies high density detection data as detection data inside the forward projected high density region.

8. The imaging apparatus as defined in claim 2, wherein the moving unit is moves the radiation source and the region of interest relative to each other along a helical trajectory, wherein the high density region is located off-center with respect to a central longitudinal axis of the helical trajectory, wherein the helical trajectory longitudinally centers the high density region with respect to portions of windings of the helical trajectory having the shortest distance to the high density region.

9. An image generation device for generating an image of a region of interest from detection data, the detection data being dependent on radiation after having traversed the region of interest, the radiation for traversing the region of interest being generated by a radiation source, the radiation source and the region of interest being moved relative to each other, while the detection data are generated, wherein the image generation device comprises:
    an identification unit for identifying in the detection data high density detection data, which depend on radiation, which has traversed a high density region having a density larger than a predefined density, and for identifying in the detection data non-high density detection data, which depend on radiation, which has not traversed the high density region,
    a density weighting unit for density weighting the detection data, wherein at least a part of the high density detection data has a smaller density weight than the non-high density detection data,
    a reconstruction unit for reconstructing an image of the region of interest from the weighted detection data.

10. An imaging method for generating an image of a region of interest, the imaging method comprising following steps:
    generating radiation for traversing the region of interest by a radiation source,
    generating detection data, which depend on the radiation after having traversed the region of interest,
    moving the radiation source and the region of interest relative to each other, while the detection data are generated,
    identifying in the detection data high density detection data, which depend on radiation, which has traversed a high density region having a density larger than a predefined density, and non-high density detection data, which depend on radiation, which has not traversed the high density region,
    density weighting the detection data, wherein at least a part of the high density detection data has a smaller density weight than the non-high density detection data,
    reconstructing an image of the region of interest from the weighted detection data.

11. Hardware storing image generation computer program for generating an image of a region of interest, the computer program comprising program code means for causing an imaging apparatus for generating an image of a region of interest comprising:
    a radiation source for generating radiation for traversing the region of interest,
    a detection unit for generating detection data, which depend on the radiation after having traversed the region of interest, a moving unit for moving the radiation source and the region of interest relative to each other, while the detection data are generated,
    an identification unit for identifying in the detection data high density detection data, which depend on radiation, which has traversed a high density region having a density larger than a predefined density, and for identifying non-high density detection data, which depend on radiation, which has not traversed the high density region,
    a density weighting unit for density weighting the detection data, wherein at least a part of the high density detection data has a smaller density weight than the non-high density detection data, and
    a reconstruction unit for reconstructing an image of the region of interest from the weighted detection data, to carry out the steps of the imaging method as defined in claim 10, when the computer program is run on a computer controlling the imaging apparatus.

12. The method as defined in claim 10, wherein the radiation has the shape of a cone beam.

13. The method as defined in claim 10, wherein the density weighting comprises multiply the detection data with density weighting factors, which depend on a line integral through the high density region along a line from the radiation source to a respective detection datum, wherein the density weighting factor is larger, if the line integral is smaller.

14. The method as defined in claim 10, further comprising determining the high density region.

15. The imaging apparatus as defined in claim 14, wherein the determining of the high density region is based on a scanogram.

16. An image generation method for generating an image of a region of interest from detection data, the detection data being dependent on radiation after having traversed the region of interest, the radiation for traversing the region of interest being generated by a radiation source, the radiation source and the region of interest being moved relative to each other, while the detection data are generated, wherein the image generation method comprises following steps:
    identifying in the detection data high density detection data, which depend on radiation, which has traversed a high density region having a density larger than a predefined density, and identifying non-high density detection data, which depend on radiation, which has not traversed the high density region,
    density weighting the detection data, wherein at least a part of the high density detection data has a smaller density weight than the non-high density detection data,
    reconstructing an image of the region of interest from the weighted detection data.

17. Hardware storing image generation computer program for generating an image of a region of interest, the computer program comprising program code means for causing an image generation device for generating an image of a region of interest from detection data, the detection data being dependent on radiation after having traversed the region of interest, the radiation for traversing the region of interest being generated by a radiation source, the radiation source and the region of interest being moved relative to each other, while the detection data are generated, wherein the image generation device comprises:
- an identification unit for identifying in the detection data high density detection data, which depend on radiation, which has traversed a high density region having a density larger than a predefined density, and for identifying in the detection data non-high density detection data, which depend on radiation, which has not traversed the high density region,
- a density weighting unit for density weighting the detection data, wherein at least a part of the high density detection data has a smaller density weight than the non-high density detection data,
- a reconstruction unit for reconstructing an image of the region of interest from the weighted detection data, to carry out the steps of the image generation method as defined in claim 16, when the computer program is run on a computer.

18. An image generation device for generating an image of a region of interest from detection data, the detection data being dependent on radiation after having traversed the region of interest, the radiation for traversing the region of interest being generated by a radiation source, the radiation source and the region of interest being moved relative to each other, while the detection data are generated, wherein the image generation device comprises:
- an identification unit for identifying from the detection data high density radiation, which has traversed a high density region having a density larger than a predefined density and which corresponds to high density data, and for identifying non-high density radiation, which has not traversed the high density region and which corresponds to non-high density data;
- a density weighting unit for density weighting the detection data, wherein at least a part of the high density radiation, which corresponds to high density detection data, has a smaller density weight than the non-high density radiation, which corresponds to non-high density detection data; and
- a reconstruction unit for reconstructing an image of the region of interest from the weighted detection data.

19. An image generation method for generating an image of a region of interest from detection data, the detection data being dependent on radiation after having traversed the region of interest, the radiation for traversing the region of interest being generated by a radiation source, the radiation source and the region of interest being moved relative to each other, while the detection data are generated, wherein the image generation method comprises following steps:
- identifying from the detection data high density radiation, which has traversed a high density region having a density larger than a predefined density and which corresponds to high density data, and non-high radiation, which has not traversed the high density region and which corresponds to non-high density data;
- density weighting the detection data, wherein at least a part of the high density radiation, which corresponds to high density detection data, has a smaller density weight than the non-high density radiation, which corresponds to non-high density detection data; and reconstructing an image of the region of interest from the weighted detection data.

* * * * *